United States Patent [19]

Collins et al.

[11] Patent Number: 4,577,042

[45] Date of Patent: Mar. 18, 1986

[54] HOMOGENEOUS COORDINATION COMPOUNDS AS OXIDATION CATALYSTS

[75] Inventors: Terrence J. Collins, Pasadena; Fred C. Anson, Altadena, both of Calif.; Stephen L. Gipson, Florissant, Mo.; Terry E. Krafft, Greeley, Colo.

[73] Assignee: California Institute of Technology, Pasadena, Calif.

[21] Appl. No.: 476,364

[22] Filed: Mar. 17, 1983

[51] Int. Cl.$^4$ ................... C07C 103/24; C07C 103/38
[52] U.S. Cl. ..................................... 564/158; 558/415; 564/159; 556/42; 556/51; 556/57; 556/45; 556/81; 556/113; 556/130; 556/136; 556/148; 556/181
[58] Field of Search ............................. 564/158, 159; 260/465 D

[56] References Cited

U.S. PATENT DOCUMENTS

| | | | |
|---|---|---|---|
| 4,009,208 | 2/1977 | Lesher | 564/158 |
| 4,049,713 | 9/1977 | Spivack | 564/158 |
| 4,051,196 | 9/1977 | Wells et al. | 564/158 X |
| 4,104,287 | 8/1978 | Fisher et al. | 564/185 X |
| 4,246,198 | 1/1981 | Rosenberger et al. | 564/158 |

*Primary Examiner*—Thomas A. Waltz
*Attorney, Agent, or Firm*—Marvin E. Jacobs

[57] ABSTRACT

A complex of a tetradentate tetraanionic ligand L of the formula:

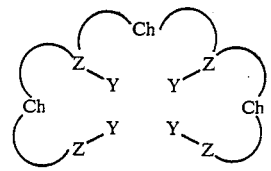

and a metal, preferably a transition metal, is described. The chelate and ring Z-CH-M-Z functional groups Z, such as N or O are resistant to oxidation and the ring contains 4 to 7 preferably 5 to 6 chain atoms. An osmium complex containing two pyridine ligands is an oxidation catalyst. Further activation by anodic oxidation and heating to a temperature exceeding 30° C. greatly increases catalytic activity.

3 Claims, 3 Drawing Figures

I

II

III

IV

V

VI

VII

HOMOGENEOUS COORDINATION COMPOUNDS AS OXIDATION CATALYSTS

ORIGIN OF THE INVENTION

The invention described herein was made in the performance of work under contracts with the National Science Foundation and is subject to the provisions of the National Science Foundation Act.

DESCRIPTION

1. Technical Field

The present invention relates to metal chelate complexes and more particularly, to novel, high oxidation state transition metal complexes bearing multidentate multianionic ligands as oxidation catalysts for organic synthesis.

2. Background Art

Among the variety of agents for oxidation of organic compounds the most commonly used are derivatives of hexavalent chromium and heptavalent manganese. In terms of their role in elementary kinetic steps, metal ion oxidants usually function as either one or two equivalent reagents. One electron oxidants are those that accept a single electron by direct transfer or by interaction with a hydrogen or halogen atom. Cases have been made for two equivalent oxidants accepting two electrons simultaneously from the substrate; alternatively they accept a hydride ion or lose an oxygen atom. When permangante or chromium (VI) compounds behave as oxidizing agents, the reaction mechanisms are typically very complex. The probable source of selectivity problems with these reagents is that they are in fact best considered to be a family of oxidizing agents rather than a pure reagent. The diversity of chemistry possible in their redox reactions makes for poor selectivity. One very convincing illustration of this point comes from the Cr(VI) oxidation of cyclobutanol. The final inorganic product from the Cr(VI) oxidation of cyclobutanol is Cr(III). Cr(VI) oxidizes cyclobutanol to cyclobutanone.

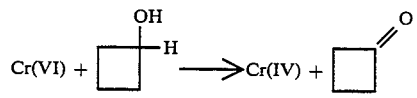

However, n intermediate Cr(IV) leads to ring cleavage to afford the organic product $HOCH_2CH_2CH_2CHO$. Another substrate susceptible to cleavage during chromic acid oxidation is illustrated below:

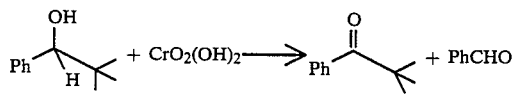

An intermediate Cr(IV) complex causes cleavage of the C—C bond to yield PhCHO and $(CH_3)COH$. The cleavage processes can be suppressed by addition of stoichiometric quantities of manganese (II), catalytic amounts of cerium (II) or cerium(IV), or stoichiometric addition of oxalic acid which intercept the Cr(IV).

Even for ostensibly simple processes where clean reactions occur, complex menchanisms underly the transformations. The oxidation of isopropyl alcohol in 97% acetic acid proceeds by the following sequence of events.

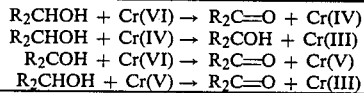
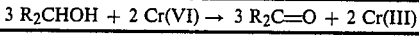

Both Cr(IV) and Cr(V) enter into the isopropanol oxidation process.

Whereas the permanganate oxidation of a primary alcohol to an acid, for instance, will proceed via a series of one or two electron steps, the final metalloproduct is manganese dioxide (or manganese(II) in acid media), corresponding to a three (or five) electron change at the metal. Clearly, intermediate states are involved in the redox process. Permanganate is not a good candidate for oxidizing a secondary alcohol to a ketone, since the reaction is accompanied by carbon-carbon cleavage. Isopropanol oxidation, for instance, leads to formic acid, acetic acid, carbon dioxide, and acetone as reaction products. It seems to be very likely that a major reason for this poor selectivity is that many oxidizing agents are produced in going from Mn(VII) to Mn(IV) or Mn(II).

Clearly one should not describe permanganate or chromium(VI) oxo reagents as single oxidizing agents, but rather each reagent is, in addition to inherently being an oxidizing agent, the precursor to other reagents generated in situ. Rather surprisingly, little attention has been directed to employing manganese(VII) and chromium (VI) as other than "off-the-shelf" reagents, that is to creating new oxido species in order to obtain reactivity and specifity different from that of the parent compounds. There are a large number of studies that have focused on the use of chromium(VI) in different readily available media. Some of the most useful easily prepared oxidizing agents have been discovered in these studies. Each of these reagents exhibits different selectivity and offers different advantages. Examples include Jones' reagent (chromic acid in acetone), Sarett's reagent ($CrO_3$ in pyridine solvent), Collins' reagent ($CrO_3(py)_2$ in dichloromethane). Sharpless' reagent ($CrO_2Cl_2$, tertiary butanol and pyridine in dichloromethane) and $CrO_3$/HMPT.

It should be pointed out that there are a number of selective oxidation reactions involving inorganic oxo-containing reagents—e.g.

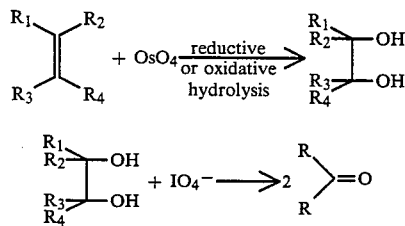

Both reactions are usually very high yielding. In each case the reaction is also selective at the inorganic component. The clean formal two electron processes Os(VIII)→Os(VI) and $IO_4^-→IO_3^-$ are all that occur.

STATEMENT OF THE INVENTION

The present invention provides a new class of metallo-organic oxidizing agents that are capable of exhibiting much greater selectivity than traditional metal-oxo complexes. It is believed that the metal ions in the oxidizing agents of the invention undergo controlled reduction from a higher state to only one lower state. This controlled redox transition leads to selectivity in the oxidation of organic substrates. In fact, the reaction can be so slective that thermodynamically unfavorable intermediates are prepared, such as the oxidation of an alcohol to an aldehyde rather than to a carboxylic acid.

From a study of metallo-oxo reagents, it was determined that non-selectivity can be attributed to failure to control redox changes at transition metal sites during redox reactions. It was then postulated that stabilization of higher oxidation states might lead to selective oxidation systems, especially if systems could be generated where control of redox changes at the metal site could be achieved in oxidation reactions to give clean two electron changes.

Complexing the transition metal with a chelating ligand is a potential route to change the coordination environment of high valent oxo complexes by tying up binding sites and preventing oxidation reactions by lower valent metal ion intermediates. Readily available multidendate ligands are unsuitable for various reasons, such as insufficient negative charge or sensitivity to oxidation as with EDTA.

Stabilized, selective oxidizing agents in accordance with the invention are complexed with a tetradendate, tetraanionic ligand L of the formula:

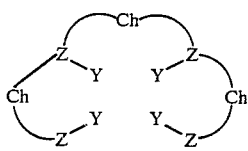

where Z is an anionic oxidation resistant metal complexing group, such as N or O, and Z-Ch-Z forms an oxidation resistant 4 to 7 membered chelate ring with a metal, preferably a 5 to 6 member ring and Y is any other atom, such as hydrogen. When the ligand is in the neutral form, the ligand can be denoted $LH_4$. All of the Z anions may be in the same equatorial plane.

The metal chelate has the following formula:

$$LMX_n$$

where n is 0, 1, 2 or 3 and X is any other ligand such as a Lewis base, oxygen, halide, etc. The Lewis base should survive activation by anodic oxidation. Examples of suitable Lewis bases are monodendate nitrogen bases such as pyridine. The active catalyst may have at least one vacant coordination site or such a site may form during catalytic oxidation. M is a metal selected from Group III-VIII of the Periodic Table. The metal M is preferably a transition metal but can also be any atom behaving as a metal, such as iodine in its heptabalent state. Exemplary transition metals are Sc, Ti, V, Cr, Mo, W, Mn, Tc, Re, Fe, Ru, Os, Co, Rh, Ir, Pd, Pt, Ag, Au and Zn, but the most useful metals appear to be V, Cr, Mn. Fe, Ru and Os.

Ch represents an oxidation resistant ligand chain which can be homocarbon or heterocarbon, but should contain 1 to 4 chain atoms. The heterogroups can be selected from N, $SO_2$, O, Si, P, etc. X can be monodentate ligands such as oxo, imido (=NR where R is any organogroup), nitrido or neutral ligands such as pyridine.

The ligands —ZChZ— should have the following properties:

1. Negative charge sufficient to counter the high positive charge of an oxidized center;
2. Insensitivity to oxidation;
3. Chemically innocent binding sites that are insensitive to hydrolysis;
4. The formation of 4–7, preferably 5- or 6- membered metallocycles upon completion in order to obtain mononuclear complexes that avoid polymerization;
5. The provision of an empty coordination site in the resulting metallo complex to allow the substrate being oxidized to coordinate to the metal prior to oxidation;
6. An ability to change the donor properties of the multidentate ligand in order to provide controlled and selective oxidation power in the metallo complex.

Other preferred features are sufficient molecular flexibility to allow the chelate complex to form as desired and ligands that can be provided by direct and simple synthesis.

These and many other features and attendant advantages of the invention will become apparent as the invention becomes better understood by reference to the following detailed description when considered in conjunction with the accompanying drawings.

DETAILED DESCRIPTION OF THE INVENTION

The transition metal oxidizing agents have both sigma bonds and weak pi bonds. The multidendate polyanion of the invention surrounds the positively charged metal with a jacket of negative charge. Oxidizable functional groups such as primary amine or alcohol should be avoided.

A class of tetradentate, tetra-anionic ligands are illustrated by the formula:

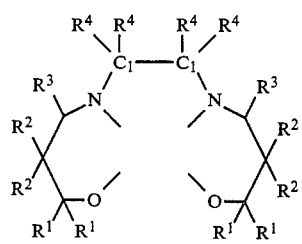

where
$R^1$ is F or $CF_3$, aliphatic or aromatic;
$R^2$ is H or aliphatic; and
$R^1$ and $R^2$ can be combined to form an aromatic group, such as benzene protected by electron withdrawing, substituent groups, such as Cl, F, $NO_2$, CN or a sterically hindered group, such as t-butyl;
$R^3$ is O or NR; and $R^4$ is hydrogen or aliphatic, such as alkyl groups of 1 or more carbon atoms, or the $R^4$ groups are replaced by one aromatic ring linking their adjoining atoms $C_1$ and $C_2$.

Figure 1:
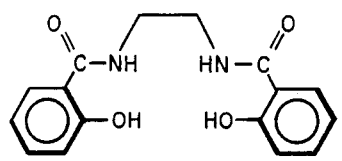
FIG. 1 illustrates a family of multidendate, multianionic ligands of the invention.
Figure 1:
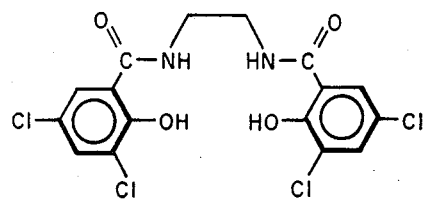
Figure 1:
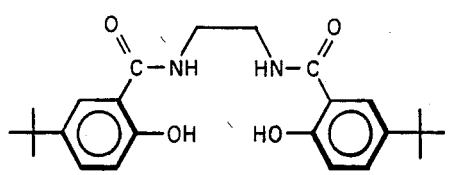
Figure 1:
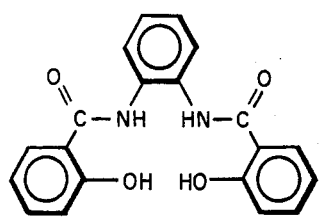
Figure 1:
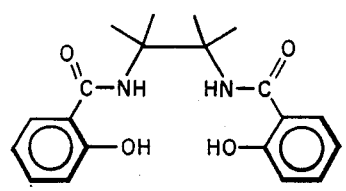
Figure 1:
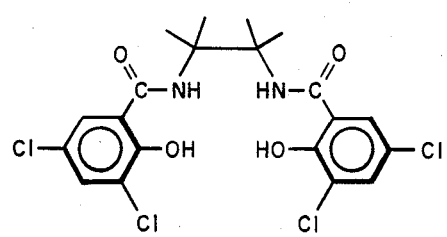
Figure 1:
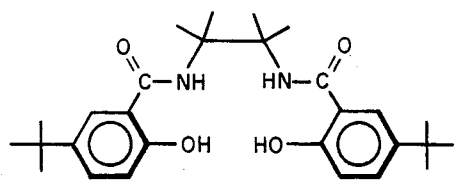

Representative compounds are listed in the following table and are illustrated in FIG. 1.

TABLE 1

| COMPOUND | EMPIRICAL FORMULA |
|---|---|
| I | N,N'—bis(2-hydroxybenzamido)-1,2-ethane[(H)₄HBA—Et] |
| II | N,N'—bis(3,5-dichloro-2-hydroxy-benzamido)-1,2-ethane [(H)₄CHBA—Et] |
| III | N,N'bis(5-t-butyl-2-hydroxy benzamido)-1,2-ethane [(H)₄-t-BuHBA—Et] |
| IV | N,N'—bis(2-hydroxybenzamido)-1,2-benzene [(H)₄HBA—OBz] |
| V | N,N'—bis(2-hydroxy-benzamido)-2,3-(2,3-dimethyl butane) [(H)₄CHBA—DMBu] |
| VI | N,N'—bis(3,5-dichloro-2-hydroxy-benzamido)-2,3-(2,3-dimethyl butane) [(H)₄CHBA—DMBu] |
| VII | N,N'—bis(5-t-butyl-2-hydroxy-benzamido)-2,3-(2,3-dimethyl butane) [(H)₄-t-BuHBA—DMBu] |

The synthesis of these tetradendate ligands is shown in Table 2.

TABLE 2

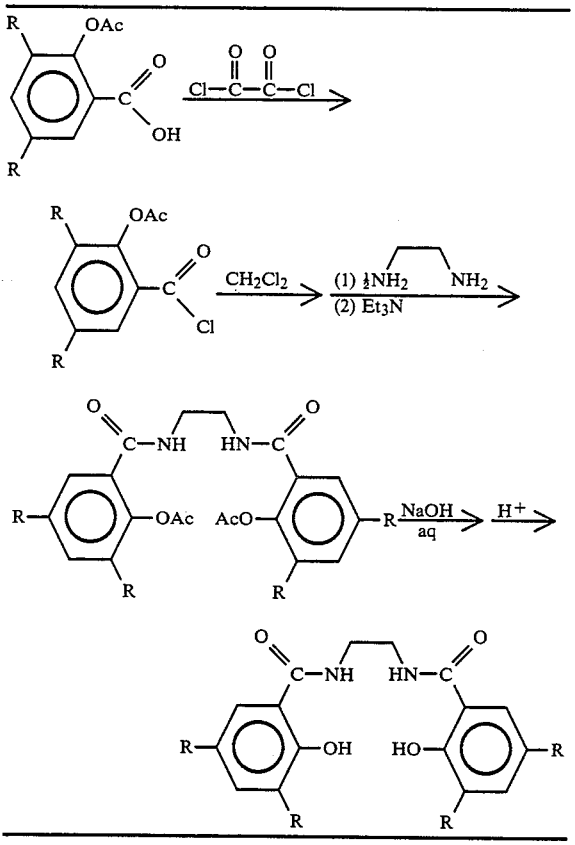

The o,p-dichlorinated phenol rings utilized in compounds II and VI of TABLE 1 are believed to provide increased oxidation resistance. The benzene ring may be trichlorinated, if necessary. Furthermore, the high oxidation state metal centers to which the phenol rings are bound should be electron-withdrawing, thus reducing activation by lone pairs on the phenol oxygen.

The ligands in TABLE 1 and FIG. 1 were synthesized as follows:

EXAMPLE 1

Preparation of [(H)₄HBA-Et]. 2-acetyl salicylic acid (50.0 g., 0.277 mole) is warmed for four hours in 50–60 mils. of neat oxalyl chloride. The initial slurry gradually changes to a pale yellow solution as the acid is converted to the acid chloride. NOTE: This reaction must be well ventilated since large quantities of HCl and CO gas are produced. When gas evolution has ceased, the remaining oxalyl chloride is distilled off in vacuo. The residue is dissolved in 30 mls. of dry dichloromethane which is also distilled off in vacuo; this step is repeated several times to remove the last traces of oxalyl chloride. The product is dissolved in 100 mls. of dry dichloromethane and refigerated. A solution of ethylene diamine (9.277 mls., 0.138 mole) and 100 mls. of dry dichloromethane is placed in a 500 ml. round bottom flask equipped with a stir bar which is immersed in an ice bath. After the solution has cooled sufficiently, the freshly prepared acid chloride solution is slowly dripped in with stirring. The slurry is stirred for one hour at which time an excess of one equivalent of triethylamine is added; the mixture is stirred for an additional one-half hour. This mixture is then treated with ca. 100 mls. of warm 6 M NaOH and heated in vacuo to distill off the dichloromethane and triethylamine. The remaining aqueous solution is decanted from the undissolved organic residues which are then dissolved in a minimal amount of acetone and treated with an additional 50 mls. of warm 6 M NaOH. The acetone is then distilled off in vacuo and the aqueous portions are combined. This very basic solution is cooled on ice, and is then cautiously acidified with concentrated HCl. The product, [(H)₄HBA-Et], precipitates and is easily collected. The recrystallized yield (from acetone-water) is 80%.

Preparation of [(H)₄HBA-oBz], [(H)₄HBA-DMBu], and [(H)₄t-Bu-HBA-Et]. The ligands N,N'-bis(2-hydroxybenzamido)-1,2-benzene, [(H)H₄HBA-oBz], N,N'-bis(2-hydroxybenzamido)-2,3-(2,3-dimethylbutane), [(H)₄HBA-DMBu], and N,N'-bis(5-t-butyl-2-hydroxybenzamido)-1,2-ethane, [(H)₄t-BuHBA-Et], are all synthesized in an analogous manner to that of N,N'-bis(2-hydroxybenzamido)-1,2-ethane, [(H)₄HBA-Et], described above. TABLE 3 lists the starting materials, recrystallizing solvents, and yields for these preparations.

Preparation of [(H)₄CHBA-Et]. [(H)₄HBA-Et] (5 grams) is dissolved in 80–100 mls. of warm glacial acetic acid. Chlorine gas is bubbled through the solution for a one-half hour period; the product precipitates during this time due to its low solubility in acetic acid. The mixture is then cooled on ice. The product is collected on a glass frit and washed with cold water. It is easily recrystallized from an acetone-water system. The overall yield is ca. 90%.

TABLE 3

| LIGAND | STARTING MATERIAL | RECRYSTALLIZING SOLVENTS | YIELD |
|---|---|---|---|
| [(H)₄HBA—Et] | 2-acetyl salicylic acid; ethylenediamine | acetone/water | 80% |
| [(H)₄HBA—OBz] | 2-acetyl salicylic | acetone/ | 81% |

TABLE 3-continued

| LIGAND | STARTING MATERIAL | RECRYS-TALLIZ-ING SOLVENTS | YIELD |
|---|---|---|---|
| | acid; O—phenylene-diamine | water | |
| [(H)₄HBA—DMBu] | 2-acetyl salicylic acid; 2,3-diamino-2,3-dimethylbutane | DMF/water | 56% |
| [(H)₄t-BuHBA—Et] | 5-t-butyl-2-acetyl salicylic acid; ethylenediamine | acetone/water | 50% |

The ligand family forms complexes with numerous metal centers. It is a simple matter to coordinate the ligands in a tetradentate fashion with Fe(III) and Cr(III) to produce anionic complexes according to the following reaction:

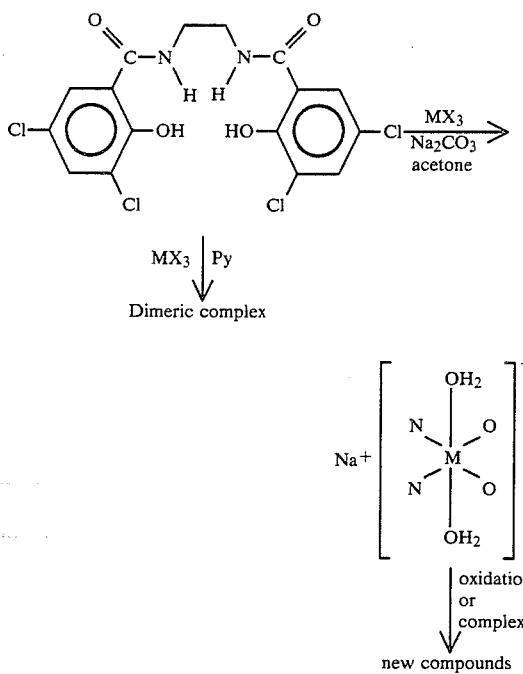

The compounds have been characterized by elemental analysis (C, H, ±0.4%) ir and room temperature magnetic susceptibility. The planar tetradentate tetraanionic coordination type exhibits a characteristic ir spectrum in the amide region (1500–1650 cm$^{-1}$). The ligand complexation type is dependent on the method of synthesis for chromium complexes. When insertion from chromium(III) chloride hexadydrate is performed in acetone using sodium carbonate as base, monomeric complexes are believed to be obtained. When pyridine is the solvent a complex with a distinctive ir spectrum is obtained. An X-ray crystal structure determination of this molecule has shown it to be a dimeric complex. This interesting molecule exhibits both types of monodentate amido coordination to the same metal, viz O-coordination as a neutral ligand and N-coordination as an anionic ligand. This is the first structure of N-amide coordination to chromium(III).

An osmium complex of ligand II was prepared as follows:

EXAMPLE 2

Treatment of a blue methanol solution of the salt, K$_2$[Os(OH)$_4$(O)$_2$], with a colorless solution of the ligand I, results in a color change to deep orange. Removal of solvent followed by recrystallization from ethanol/diethyl ether affords high yield of the orange microcrystalline salt K$_2$[OsO$_2$—(CHBA)-Et].H$_2$O as shown in the following reaction:

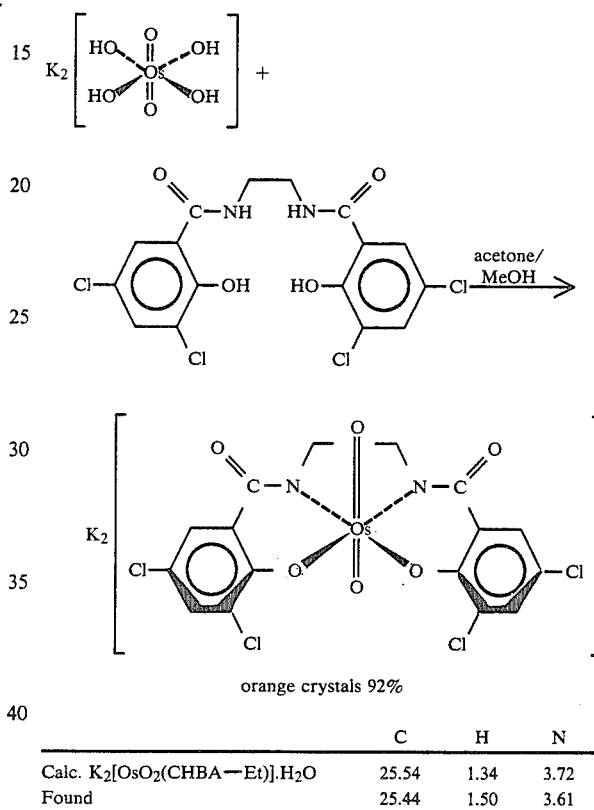

orange crystals 92%

| | C | H | N |
|---|---|---|---|
| Calc. K$_2$[OsO$_2$(CHBA—Et)].H$_2$O | 25.54 | 1.34 | 3.72 |
| Found | 25.44 | 1.50 | 3.61 |

This Os(VI) complex reacts with triphenylphosphine (2.5 equivalents) in pyridine/water to give a red compound which reacts with hydrogen peroxide in THF at 0° C. to produce a deep blue neutral crystalline complex (60% based on K$_2$[Os(OH)$_4$O$_2$]) after addition of methanol and removal of the THF as shown in the following reaction scheme:

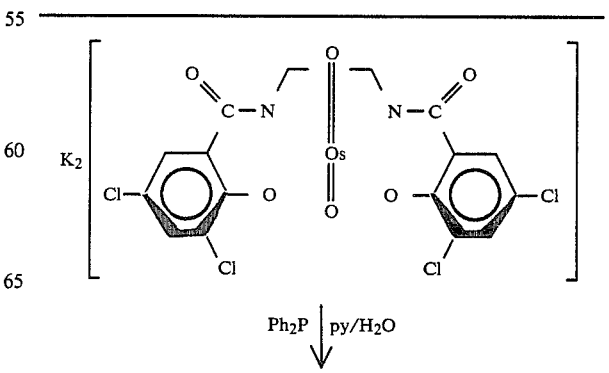

-continued

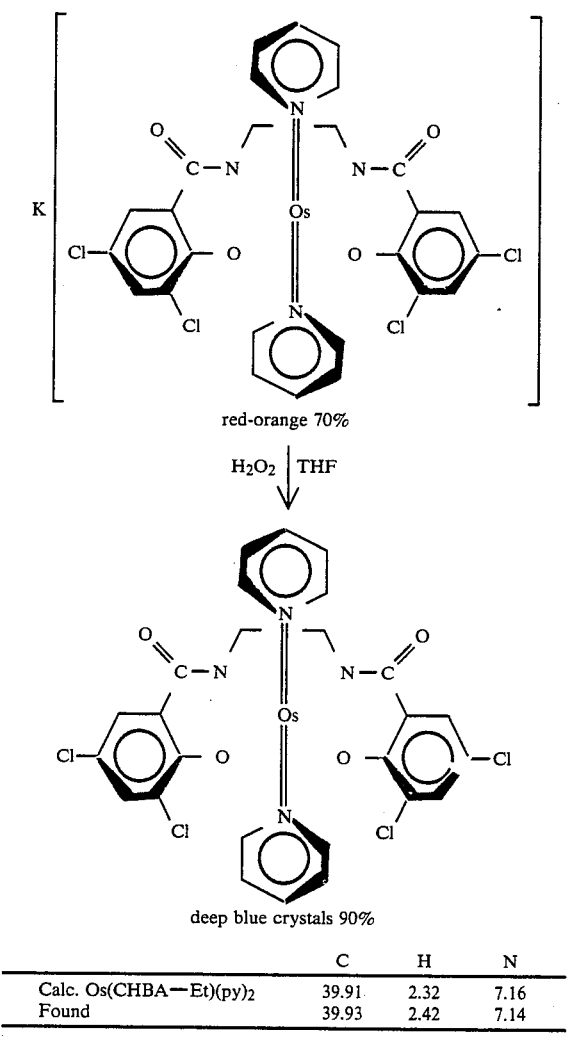

red-orange 70%

H₂O₂ | THF deep blue crystals 90%

|  | C | H | N |
|---|---|---|---|
| Calc. Os(CHBA—Et)(py)₂ | 39.91 | 2.32 | 7.16 |
| Found | 39.93 | 2.42 | 7.14 |

Figure 2:
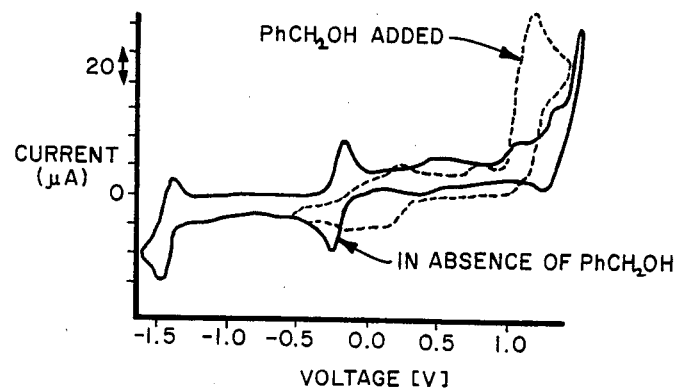
FIG. 2 is a set of graphs showing the electrochemical oxidation of benzyl alcohol by a bis pyridine osmium CHBA complex.

The electrochemical behavior of Os($\eta^4$-CHBA-Et)(py)₂ in dichloromethane with [NBu₄][ClO₄] as supporting electrolyte using a basal plane graphite electrode is shown in FIG. 2. Two chemically reversible reduction waves apprear at −0.2 V and −1.45 V (versus SSCE), and two electrochemically irreversible oxidation waves (scan rate=200 mV s⁻¹) appear in the region of 1.0 V.

The two electrochemically reversible reduction couples define the existence of the osmium (III) and osmium (II) complexes [Os($\eta^4$-CHBA-Et) (py)₂]⁻/². On addition of benzyl alcohol a small, apparently catalytic wave develops at 1.3 V.

The catalytic oxidation activity of the blue paramagnetic complex Os($\eta^4$-CHBA-Et) (py)₂ is greatly increased by anodic oxidation of the complex in a nonpolar, aprotic solvent followed by heating the complex to a temperature of at least 30° C. as shown in the following reaction scheme.

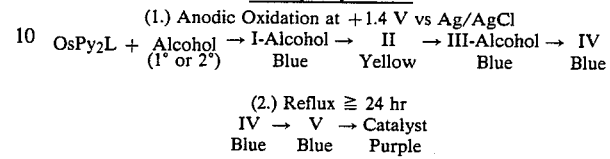

Catalyst Synthesis
(1.) Anodic Oxidation at +1.4 V vs Ag/AgCl

Figure 3:
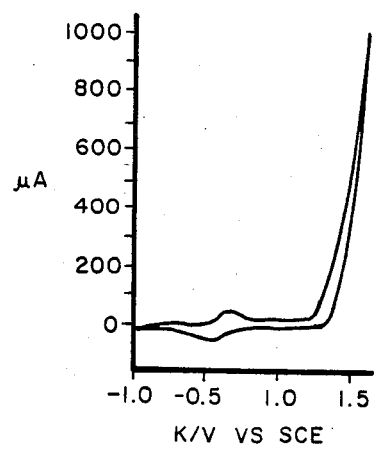
FIG. 3 is a cyclic voltammogram of highly active osmium catalyst in resence of benzyl alcohol.

OsPy₂L + Alcohol → I-Alcohol → II → III-Alcohol → IV
(1° or 2°)   Blue         Yellow    Blue         Blue (2.) Reflux ≧ 24 hr
IV → V → Catalyst
Blue Blue Purple A new purple ligand complex is produced which shows a dramatic wave is the cyclic voltammogram in the presence of primary and secondary alcohols (FIG. 3). During the course of producing this new catalyst, five additional products form and decay as demonstrated by TLC. Conversion to the active catalyst in quantitive as judged by TLC. The highly active blue catalyst can be treated by column chromatography without loss of activity which argues against the possibility that pretreatment produces some small quantity of an active impurity with the bulk material being inactive. Osmium tetraoxide is not the catalyst as demonstrated by blank experiments. The highly active final blue compound still contains a CHBA ligand and the to pyridine ligands. It has a positive charge of 1 or 2.

Bulk electrolysis (at 1.4–1.6 V) at either a reticulated vitreous carbon or a basal graphite of a benzyl alcohol containing solution in dichloromethane with tetra-n-butyl ammonium perchlorate as supporting electrolyte results in conversion of benzyl alcohol to benzaldehyde. Benzaldehyde is not oxidized to benzoic acid or benzyl benzoate. This statement means that no acid or ester can be detected in the oxidized solution and that if an oxidation is attempted using 0.5 M benzaldehyde and 40 μM catalyst in the absence of benzyl alcohol no catalytic current is observed. Current efficiencies for benzaldehyde formation are 100–102% as measured by HPLC. It has been found the HPLC is the best analytical method, but glc and the spectrophotometric determination of the 2,4-dinitrophenylhydrazone derivative have also been utilized. Fifty equivalents of benzyl alcohol were oxidized in two hours. The work was conducted with low concentrations of catalyst (40 μM) and 0.5 benzyl alcohol in bulk electrolysis experiments.

TABLE 4

| Controlled Potential Oxidations of 40 μM Catalyst + 0.5 M Alcohol | | | | | | |
|---|---|---|---|---|---|---|
| Expt. # | Alcohol | Solvent | Potential | Time (hr) | mol Aldehyde / mol Catalyst | CE (%) |
| 1 | Benzyl | CH₂Cl₂ | +1.40 | 6.3 | 52 | 102 |
| 2 | " | " | +1.50 | 4.0 | 62 | 106 |
| 3 | " | " | +1.60 | 2.25 | 53 | 103 |
| 4 | " | MeCN (He sat.) | +1.60 | 4.5 | 23 | 88 |
| 5 | " | MeCN (O₂ sat.) | +1.60 | 4.5 | 26 | 89 |
| 6 | n-Butyl | CH₂Cl₂ | +1.50 | 0.6 | 6* | |

*Estimated from Charge consumed.

What is most remarkable about this system is its extraordinarily high selectivity for primary alcohol oxidation to aldehyde without further oxidation to the acid or ester. Less than 1% of aldehyde oxidation occurs in typical experiments as described above. In itself, this selectivity is not surprising since after the oxidation of fifty equivalents the ratio of benzyl alcohol to benzaldehyde is 250 and the rate of benzaldehyde oxidation would need to be commensurately greater than that for benzyl alcohol in order to observe any oxidation. However, when the oxidation of 0.5 M benzaldehyde in the presence of 50 μM catalyst is attempted, no catalytic current is observed, demonstrating that the selectivity is very considerable indeed. By comparison, recently an electrocatalytic system based on (trpy) (bpy) $RuOH_2^{2+}$/(trpy) (bpy)$RuO^{2+}$ was reported. Analysis shows that after 100 catalytic turnovers acetate and acetaldehyde are produced in about equal proportions. This further oxidation of aldehyde occurs when the ratio of alcohol to aldehyde is at least 40:1.

There have been a number of recent reports of electrochemcial oxidations of alcohols. The above mentioned ruthenium systems perform a number of very intersting oxidations including aromatic hydrocarbons and has been used for alcohol oxidation after first being attached to surface modified electrodes. A polymeric reagent electrochemically generated from cross-linked poly-4-vinylpyridine hydrobromide was found to be effective for the catalytic oxidation of secondary alcohols to ketones. Primary and secondary alcohols have been electrocatalytically oxidized to the corresponding esters and ketones in moderate to excellent yields using iodide as the catalyst source and secondary alcohols have been oxidized effectively to ketones using a thioether or thiether/bromide catalyst. The uncatalyzed anodic oxidation of primary alcohols gives product distributions that include aldehyde, acid and ester. The distributions are strongly media dependent, but very high current yields of aldehyde are not found. The electrocatalytic system of the invention is the only known system that delivers extreme current efficiency for primary alcohol oxidation to aldehyde.

The catalyst slowly deactivates. Over the course of the two hour catalytic oxidation the blue color faces and is replaced by a yellow color. It is not understood what is happening in this deactivation procedure, but it is likely that oxidative ligand decomposition is the major process.

In the absence of a reducing agent, such as an alcohol, the catalyst rapidly undergoes the color change from blue to yellow that accompanies deactivation further implicating some form of oxidative decomposition. Preliminary cyclic voltammetric data suggest that catalyst oxidations proceed with other alcohols such as methanol, n-butanol, isopropanol, sec-butanol, cyclohexanol, allyl alcohol, and n-octanol, although the catalytic waves are not as pronounced as with benzyl alcohol. A bulk electrolysis experiment was performed on n-butanol and the most significant finding was that the catalyst underwent deactivation more rapidly than with benzyl alcohol. A 40 μM catalyst concentration was employed. With 1 M n-butanol 27 electrons are passed per osmium before deactivation is complete. With 0.5 M benzyl alcohol over 105 elecrons are passed with approximately 80% loss of activity. These results reinforce the belief that an oxidizing agent is produced at the electrode that then either oxidizes an alcohol or oxidizes the ligand. The lifetime of the catalyst is dependent on the rate at which it is consumed by alcohol. Either increasing the alcohol cncentration or using more easily oxidized alcohols (benzyl instead of n-butyl) increases the catalyst lifetime. As the potential is increased from 1.4 V through 1.6 V the catalyst deactivates more rapidly. However, the same quantity of catalysis occurs in the separate experiments again reinforcing the proposed mechanism.

It is to be understood that only preferred embodiments of the invention have been described and that numerous substitutions, modifications and alterations are permissible without departing from the spirit and scope of the invention as defined in the following claims.

We claim:

1. A compound forming a tetradendate, tetraanionic ligand with a metal selected from compounds of the formula:

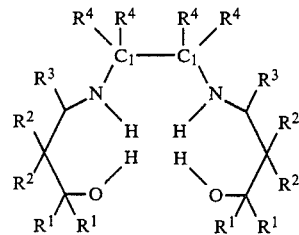

where
$R^1$ is F or $CF_3$, aliphatic or aromatic;
$R^2$ is H or aliphatic; and
$R^1$ and $R^2$ can be combined to form an aromatic group such as benzene protected by electron withdrawing, substituent groups, such as Cl, F, $NO_2$, CN or a sterically hindered group, such as t-butyl;
$R^3$ is O; and
$R^4$ is hydrogen or aliphatic, such as alkyl groups of 1 or more carbon atoms, or the $R^4$ groups are replaced by one aromatic ring linking their adjoining atoms $C_1$ and $C_2$.

2. A compound according to claim 1 selected from compounds of the formula:

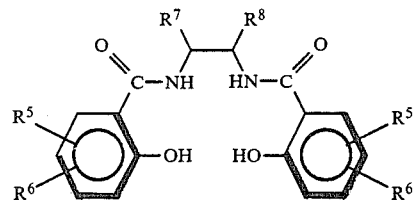

where $R^5$ and $R^6$ are individually selected from H, t-butyl or chloro and $R^7$ and $R^8$ are selected from H, T-butyl or $R^7$ and $R^8$ are bridged to form a single aromatic ring.

3. A compounding according to claim 2 selected from the group consisting of:
N,N'-bis-(2-hydroxybenzamido)-1,2-ethane;
N,N'-bis-(3,5-dichloro-2-hydroxybenzamido)-1,2-ethane;
N,N'-bis-(5-t-butyl-2-hydroxy benzamido)-1,2-ethane;
N,N'-bis-(2-hydroxybenzamido)-1,2-benzene;
N,N'-bis-(2-hydroxy-benzamido)-2, 3-(2,3-dimethyl butane);
N,N'-bis-(3,5-dichloro-2-hydroxy-benzamido)-2, 3-(2,3-dimethyl butane); or
N,N'-bis-(5-t-butyl-2-hydroxy-benzamido)-2, 3-(2,3-dimethyl butane).

* * * * *